(12) United States Patent
Draper et al.

(10) Patent No.: US 9,561,330 B2
(45) Date of Patent: Feb. 7, 2017

(54) PEN-TYPE DRUG INJECTION DEVICE WITH OPTICAL DOSE ENCODING AND DECODING SYSTEM

(71) Applicant: SANOFI-AVENTIS DEUTSCHLAND GMBH, Frankfurt am Main (DE)

(72) Inventors: Paul Richard Draper, Worcestershire (GB); Anthony Paul Morris, West Midlands (GB); Stephen Francis Gilmore, Bristol (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/760,430

(22) PCT Filed: Jan. 13, 2014

(86) PCT No.: PCT/EP2014/050466
§ 371 (c)(1),
(2) Date: Jul. 10, 2015

(87) PCT Pub. No.: WO2014/111339
PCT Pub. Date: Jul. 24, 2014

(65) Prior Publication Data
US 2015/0343150 A1    Dec. 3, 2015

(30) Foreign Application Priority Data
Jan. 15, 2013   (EP) ..................................... 13151368

(51) Int. Cl.
*G06F 17/00*       (2006.01)
*A61M 5/315*       (2006.01)
(Continued)

(52) U.S. Cl.
CPC .......... *A61M 5/31525* (2013.01); *H04L 9/321* (2013.01); *A61M 5/20* (2013.01);
(Continued)

(58) Field of Classification Search
USPC ............................. 235/375, 462.01, 462.09
See application file for complete search history.

(56) References Cited

U.S. PATENT DOCUMENTS 9,289,559 B2 *   3/2016   Pedersen ................. A61M 5/20
2011/0009821 A1 *   1/2011   Jespersen ............ A61M 5/1452
604/135

(Continued)

FOREIGN PATENT DOCUMENTS

WO    2004/009163    1/2004
WO    2010/139640    12/2010
(Continued)

OTHER PUBLICATIONS

International Search Report and Written Opinion for Int. App. No. PCT/EP2014/050466, completed May 9, 2014.

(Continued)

*Primary Examiner* — Ahshik Kim
(74) *Attorney, Agent, or Firm* — McDonnell Boehnen Hulbert & Berghoff LLP (57) ABSTRACT

A method of decoding encoded information is presented where one or more sensors are controlled to periodically check for motion of a movable component of a drug delivery device having encoded information thereon. If motion of the movable component is detected, preventing a first encoded information reading and decoding process from being performed, when motion of the movable component is not detected, performing the first encoded information reading and decoding process.

15 Claims, 4 Drawing Sheets

(51) Int. Cl.
*H04L 9/32* (2006.01)
*A61M 5/20* (2006.01)
*A61M 5/24* (2006.01)

(52) U.S. Cl.
CPC ........... *A61M 5/24* (2013.01); *A61M 5/31551* (2013.01); *A61M 2205/3306* (2013.01); *A61M 2205/3317* (2013.01); *A61M 2205/8212* (2013.01); *H04L 2209/34* (2013.01)

(56) References Cited

U.S. PATENT DOCUMENTS

2012/0053527 A1 3/2012 Cirillo
2015/0374930 A1* 12/2015 Hyde .................. A61M 5/3294
                                                                                                     604/191

FOREIGN PATENT DOCUMENTS

| WO | 2011/117212 | 9/2011 |
| WO | 2013/004843 | 1/2013 |
| WO | 2013/004844 | 1/2013 |

OTHER PUBLICATIONS

European Search Report for EP App. No. 13151368, dated Oct. 8, 2013.

* cited by examiner

PEN-TYPE DRUG INJECTION DEVICE WITH OPTICAL DOSE ENCODING AND DECODING SYSTEM

CROSS REFERENCE TO RELATED APPLICATIONS

The present application is a U.S. National Phase Application pursuant to 35 U.S.C. §371 of International Application No. PCT/EP2014/050466 filed Jan. 13, 2014, which claims priority to European Patent Application No. 13151368.1 filed Jan. 15, 2013. The entire disclosure contents of these applications are herewith incorporated by reference into the present application.

TECHNICAL FIELD

The present invention relates to a system and method for decoding encoded information within a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to decoding systems for injectors, for example hand-held injectors, especially pen-type injectors, that is to injectors of the kind that provide for administration by injection of medicinal products from a multidose cartridge.

A user undertaking self-administration of insulin will commonly need to administer between 1 and 80 International Units. A user is also required to record their dosage history. The dosage history is an important factor in calculating future doses. The dose dialled into or dispensed from the injection device may be recorded electronically. Since such devices are generally portable and have a limited power source, power conservation is an important concern.

SUMMARY

A first aspect of the invention provides a method of decoding encoded information comprising:
  controlling one or more sensors to periodically check for motion of a movable component of a drug delivery device having encoded information thereon;
  if motion of the movable component is detected, preventing a first encoded information reading and decoding process from being performed;
  when motion of the movable component is not detected, performing the first encoded information reading and decoding process.

It is advantageous for the information reading and decoding process to be performed only when the moveable component is stationary. If the moveable component is rotating, it is likely that any information captured may be inaccurate or blurred and decoding would be impaired or impossible. This also results in a power saving relative to having the sensor powered on throughout a period of motion of the moveable component.

The method may further comprise, if motion of the movable component is detected subsequent to completion of the first encoded information reading and decoding process, performing a second encoded information reading and decoding process after it is detected that the motion of the movable component has ceased. This allows subsequent motion of the moveable component to be measured without the need for the sensor to continuously perform an information reading and decoding process. Again, the information reading and decoding process is only performed when the moveable component is stationary.

Performing an encoded information reading and decoding process may comprise:
  using the one or more sensors to read the encoded information from the movable component of the drug delivery device; and
  a processor receiving signals from the one or more sensors and decoding the encoded information.

The encoded information may comprise optically encoded images. The encoded information reading and decoding process may comprise capturing one or more images of the encoded images. Alternatively, the encoded information may comprise a pattern of conductive and non-conductive regions. The encoded information reading and decoding process may comprise using a capacitive or inductive sensor to detect changes in resistance or capacitance as the conductive and non-conductive regions move past the sensor.

The method may further comprise controlling one or more light sources to illuminate the movable component of the drug delivery device during the encoded information reading and decoding process. Illuminating the moveable component only during the encoded information reading and decoding process results in power savings.

The method may further comprise controlling one or more light sources to illuminate the movable component of the drug delivery device during the periodic check for motion of the movable component. The reliability and sensitivity of the motion check may be improved if the moveable component is illuminated.

The method may further comprise, if motion of the movable component is detected during the second encoded information reading and decoding process, performing a third encoded information reading and decoding process after completion of the second encoded information reading and decoding process.

The third encoded information reading and decoding process may be performed after a check for motion of the movable component determines that the movable component is stationary. If the moveable component moves during the second encoded information reading process, the information which is read may be incomplete, inaccurate or blurred and thus the decoding may fail. The encoded information reading and decoding process is performed again so that an accurate result can be obtained.

The method may further comprise resuming controlling the one or more sensors to periodically check for motion of a movable component subsequent to completion of the first encoded information reading and decoding process. Therefore, subsequent motion is quickly detected.

Subsequent to completion of the first encoded information reading and decoding process, the frequency of the periodic check for motion of the movable component may be dependent on the length of time for which motion of the movable component is not detected. The frequency of the periodic check may be decreased as the length of time for which motion of the movable component is not detected increases.

This results in further power savings as the periodic check for motion is performed less frequently. The frequency of the period check may be restored to its original value whenever motion of the moveable component is detected. Thus power savings are made while still allowing motion to be quickly detected.

A second aspect of the invention provides a non-transitory computer-readable storage medium having stored thereon computer-readable code, which, when executed by computing apparatus, causes the computing apparatus to perform the method of the first aspect of the invention.

A third aspect of the invention provides a decoding system comprising at least one sensor configured to read encoded information from a movable component of a drug delivery device and a processor configured to:
  if motion of the movable component is detected, prevent a first encoded information reading and decoding process from being performed;
  when motion of the movable component is not detected, perform the first encoded information reading and decoding process.

It is advantageous for the information reading and decoding process to be performed only when the moveable component is stationary. If the moveable component is rotating, it is likely that any information captured may be inaccurate or blurred and decoding would be impaired or impossible. This also results in a power saving relative to having the sensor powered on throughout a period of motion of the moveable component or permanently while a device housing the decoding system is active.

The processor may be further configured to:
  if motion of the movable component is detected subsequent to completion of the encoded information reading and decoding process, perform a second encoded information reading and decoding process after it is detected that the motion of the movable component has ceased. This allows subsequent motion of the moveable component to be measured without the need for the sensor to continuously perform an information reading and decoding process. Again, the information reading and decoding process is only performed when the moveable component is stationary.

A fourth aspect of the invention provides a drug delivery device comprising a housing retaining the decoding system of the third aspect of the invention. Integrating the decoding system with the drug delivery device increases the utility of that device.

A fifth aspect of the invention provides a decoding system according to the third aspect of the invention, wherein the decoding system is part of a supplementary device configured to be attached to the drug delivery device. Implementing the decoding system in a supplementary device allows the decoding system to be applied to devices without an electronic monitoring capability, or with a less sophisticated monitoring capability.

A sixth aspect of the invention provides an apparatus configured to perform the method of the first aspect of the invention.

BRIEF DESCRIPTION OF THE DRAWINGS

Embodiments will now be described, by way of example only, with reference to the accompanying drawings, in which.

DETAILED DESCRIPTION

Figure 1:
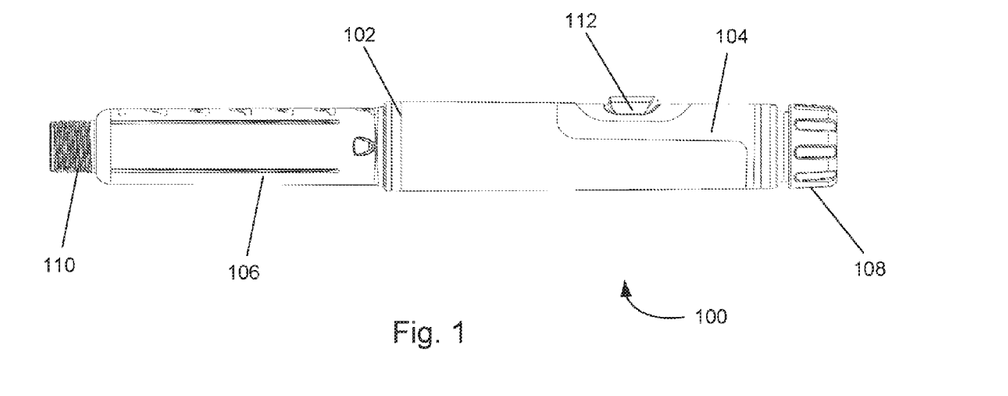
FIG. 1 shows an external view of a drug delivery device suitable for use in the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together is such a way as the drug cartridge is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a button (not shown) which must be depressed in order to deliver the set drug dose. The display 112 may be configured to display information on the drug dose which has been set and/or delivered. The display 112 may further show additional information, such as the actual time, the time of the last usage/injection, a remaining battery capacity, one or more warning signs, and/or the like.

Figure 2:
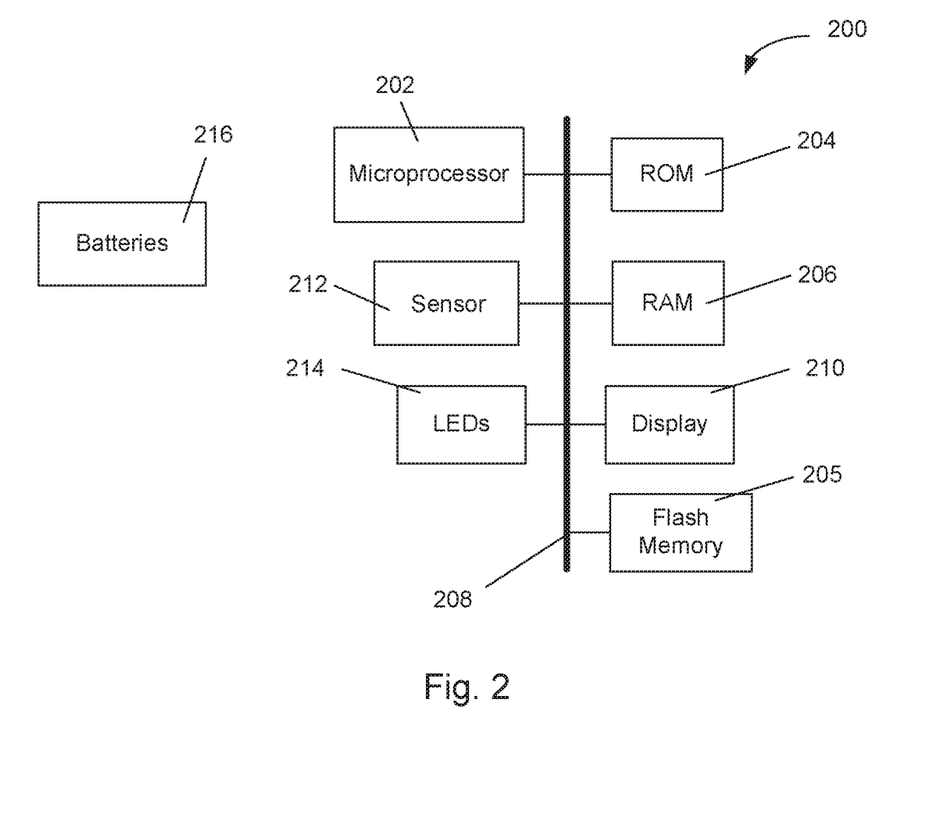
FIG. 2 shows a schematic diagram of some of the electronic components suitable for implementing the present invention.

Referring now to FIG. 2, a schematic diagram of electrical circuitry 200 forming part of the drug delivery device 100 is shown. The circuitry 200 comprises a microprocessor 202, a non-volatile memory such as a ROM 204, a writable non-volatile memory such as flash memory 205, a volatile memory such as a RAM 206, a display 210, a sensor 212, one or more LEDs 214 and a bus 208 connecting each of these components. The circuitry 200 also comprises batteries 216 or some other suitable source of power for providing power to each of the components.

The circuitry 200 may be integral with the device 100. Alternatively, the circuitry 200 may be contained within an electronic module that can be attached to the device 100. In addition, the circuitry 200 may comprise additional sensors, such as acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display 210. As such the microprocessor 202 may also comprise a display driver. The processor 202 utilises the flash memory 205 to store determined amounts of dose dialled and/or determined amounts of dose dispensed, as will be described in more detail below.

The batteries 216 may provide power for each of the components including the sensor 212. The supply of electricity to the sensor 212 and LEDs 214 may be controlled by the microprocessor 202. The microprocessor 202 may receive signals from the sensor 212 and is configured to interpret these signals. Information may be provided on the display 210 at suitable times by operation of the software/firmware and the microprocessor 202. This information may include measurements determined from the signals received by the microprocessor 202 from the sensor 212, such as the drug dose which has been set and/or delivered. The display 210 may also show additional information, such as the actual time, the time of the last usage/injection, a remaining battery capacity, one or more warning signs, and/or the like.

In some embodiments of the invention, sensor 212 is an optical sensor and is also referred to herein as optical sensor 212. The optical sensor 212 is configured to be directed at a rotatable component of the mechanism of the drug delivery device 100 and to capture images (also referred to herein as information reading). The optical sensor 212 may be configured to capture pixelated greyscale images of images or patterns printed on the rotatable component. The printed images or patterns may optically encode information. The microprocessor 202 is configured to receive the captured images from the optical sensor 212 and decode the encoded information. The one or more LEDs 214 may be used in these embodiments and are also directed at the printed images/patterns in order to provide illumination for the optical sensor 212. Alternatively, the rotatable component may have reflective and non-reflective regions printed or adhered to it. The sensor may be configured to detect the intensity patterns of reflected light.

The LEDs 214 and optical sensor 212 may be configured to operate at various wavelengths of light. The LEDs 214 and sensor 212 may, for example, operate in infra-red. The sensor 212 may have an integral LED 214, or the LEDs 214 and sensor may comprise separate units. Alternatively, a different type of light source may be used in place of the LEDs. Software stored in the ROM 204 allows the microprocessor 202 to determine from the signals received from the sensor 212 whether rotatable components is rotating.

In some other embodiments, the rotatable component may have a pattern of conductive and non-conductive regions. The sensor 212 may be a capacitive or inductive sensor configured to detect changes in resistance or capacitance as the conductive and non-conductive regions move past the sensor 212.

The circuitry 200 may comprise further components which are not shown. For example, the circuitry 200 may comprise one or more user inputs in the form of hardware or software keys. The circuitry 200 may comprise a speaker and/or a microphone. The circuitry 200 may also comprise one or more means of removing or communicating information stored in the ROM 204 or flash memory 205, such as a wireless transceiver, a card slot or a cable port (e.g. a USB port).

Figure 3:
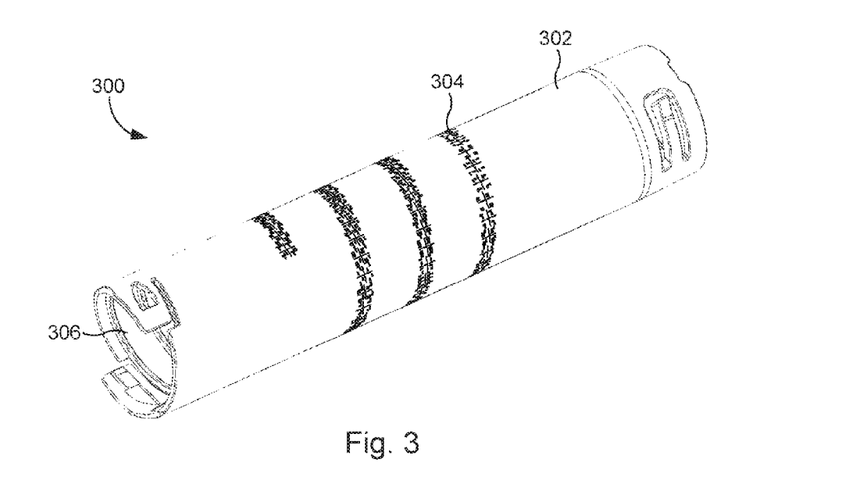
FIG. 3 shows an exemplary encoded number sleeve forming part of the drug delivery device of FIG. 1.

Referring now to FIG. 3, a perspective view of an optically encoded number sleeve 300 is shown. This optically encoded number sleeve 300 forms part of the drug dose setting and delivery mechanism internal to the first housing part 104. A detailed example of the operation of a dose setting and delivery mechanism can be found in published PCT application WO2010/139640, which is incorporated herein by reference. This document gives details of one particular drug delivery device mechanism. However, the invention may be implemented in a wide variety of different drug delivery devices having different mechanisms.

The outer surface 302 of the number sleeve 300 has a helical track 304 comprising a sequence of images. Each of the images encodes information and is designed to be viewed by the sensor 212. The drug delivery device 100 may be configured to deliver a maximum of 80 units of medicament. The track 400 may therefore comprise a series of 81 encoded images encoding positions 0 to 80.

The encoded number sleeve 300 has a helical thread 306 disposed on an inner surface. The number sleeve 300 is threaded to an inner housing part which is fixed relative to the first housing part 104. This threaded connection causes the encoded number sleeve 300 to move axially relative to the first housing part 104 when rotated i.e. when a dose is dialled into or out of the drug delivery device 100. The encoded number sleeve 300 is arranged within the mechanism such that when no dose is dialled into the drug delivery device 100 the first encoded image (encoding position "0") is located directly underneath the sensor 212. This allows the encoded image to be viewed by the sensor 212. The pitch of the track 304 is the same as the threads on the encoded number sleeve 300 and inner housing such that as the number sleeve 300 rotates and moves axially out of the first housing part 104 the track 304 remains located underneath the sensor 212.

The microprocessor 202 is configured to employ software stored in the ROM 204 to determine the content of each image, for example which parts of the image are black and which parts are white, and to identify a corresponding rotational position of the encoded number sleeve 300 relative to the sensor 212. The microprocessor 202 may achieve this by consulting a table stored in the ROM 204 which relates the content of each image to a rotational position of the number sleeve 300 and hence to a drug dose which has been dialled. Having determined the drug dose which has been dialled, the microprocessor 202 may store the result in the flash memory 205.

Figure 4:
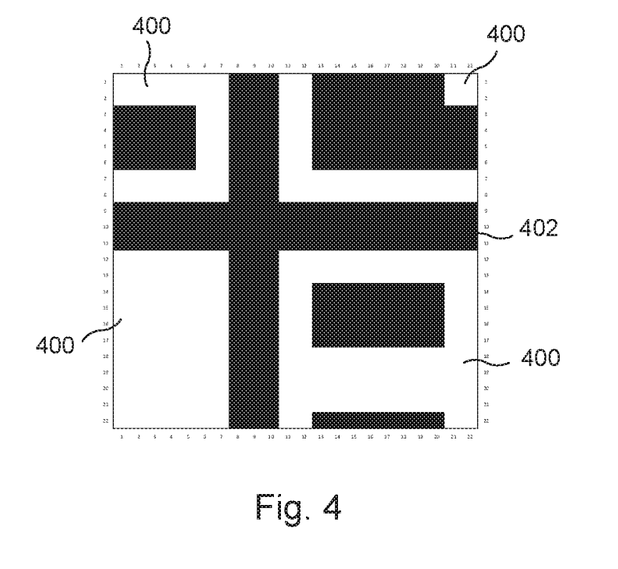
FIG. 4 illustrates an exemplary captured image from a first encoding scheme.
Figure 5:
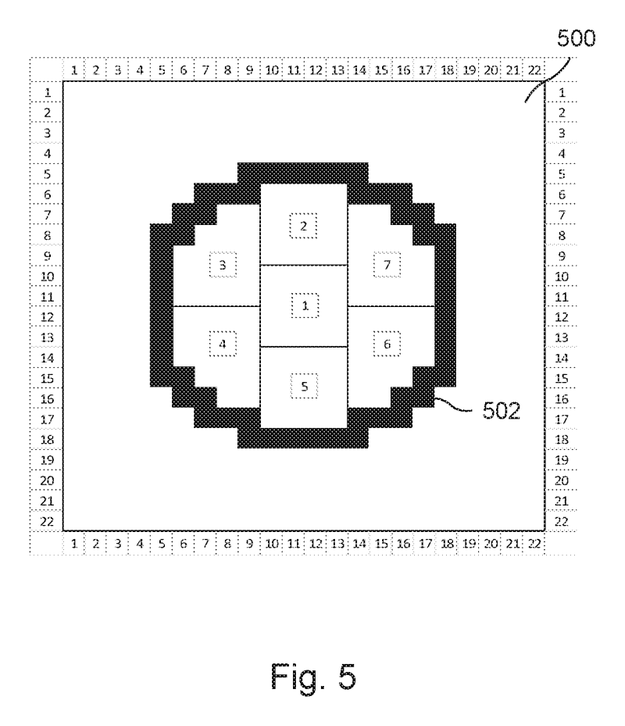
FIG. 5 illustrates a template for constructing an encoded image according to a second encoding scheme.

Referring also to FIGS. 4 and 5, two possible encoded image schemes are represented. In each of these two schemes, the images are comprised of a number of data bits which may be coloured black or white.

In the first scheme, shown in FIG. 4, an encoded image 400 is repeated in the four quadrants of a square. Only a portion of each repeated image 400 is visible in FIG. 4. The quadrants are delineated by a cross 402. The field of view of the sensor 212 is larger than any one of the repeated images, but in general is arranged to capture a portion of each of the four repeated images 400. This allows for the compensation of manufacturing tolerances which may prevent a single encoded image 400 from being viewed fully by the sensor 212. The microprocessor 202 is configured to process the received image to determine the location of the cross feature. The partially visible images 400 are then rearranged such that the full encoded image is reconstructed and can then be decoded.

FIG. 5 illustrates a template 500 for constructing an encoded image according to a second encoding scheme. This scheme comprises seven binary data bits within a circle 502. The internal area of the circle 502 is therefore split into 7 segments and each segment may be filled black to represent a "high" data bit, or white to represent a "low" data bit. In this scheme, the field of view of the sensor 212 encompasses the whole of the encoded image and captures an image containing the entire encoded image, including the circle 502. The microprocessor 202 then implements an algorithm to detect the position of the circle 502 within the image. The size of the circle 502 relative to the captured image is known, as the pattern generation and image field of view are well controlled. The algorithm therefore searches the captured image for a feature of a known shape and size.

The schemes of FIGS. 4 and 5 merely represent examples of suitable encoding schemes. The encoded image scheme may instead comprise a series of dot matrix patterns, a series of barcodes or similar or standard Arabic numerals and may comprise a single image per position or multiple repeated images. The encoded images may be printed, marked, indented, etched or similar onto the track 304.

In some alternative embodiments, the encoding scheme may not be based on optically encoded images. Instead, the outer surface 302 of the encoded number sleeve 300 may have a series of relatively conductive and relatively non-conductive regions arranged in a helical track. The sensor may be an inductive sensor or a capacitive sensor, such as a capacitive displacement sensor. A capacitive displacement sensor comprises a conductive plate. When a relatively conductive region is located underneath the sensor 212, a parallel plate capacitor is formed. The air gap between the sensor and the outer surface 302 of the encoded number sleeve 300 acts as a dielectric material. The capacitive sensor is configured to read the encoded information contained in the series of conductive and non-conductive regions. Alternatively, the sensor 212 may be a contact sensor required engagement between contacts forming the sensor 212 and the outer surface 302 of the encoded number sleeve 300, which is provided with conductive and non-conductive regions.

Figure 6:
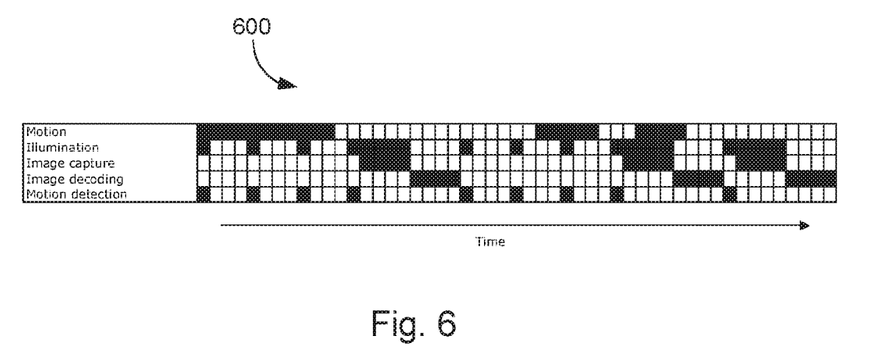
FIG. 6 is a time sequence illustrating a power saving algorithm.

As can be appreciated, the use of such electronic sensing techniques, particularly the use of optical sensors and LEDs consumes power. The drug delivery device 100 is typically a portable device powered by batteries 216 and therefore has a limited power supply. Referring now to FIG. 6, a time sequence 600 illustrating a power saving algorithm is shown.

During the normal operation of the drug delivery device 100, particularly while a user is dialling in a drug dose, the encoded number sleeve 300 may be stationary for periods of time. This may occur for a short period, for example as a user re-arranges their grip of the dial 108 to dial a larger dose size. The encoded number sleeve 300 may be stationary for a longer period, for example if the user pauses in the middle of a dialling operation in order to check their prescription, re-calculate their dose value or for any number of other reasons. Additionally, a pause occurs after dialling, but before dispensing as the user inserts the needle of the drug delivery device 100 into their skin.

The position of the encoded images on the number sleeve 300 does not change while the sleeve 300 is stationary and so an image capture operation can be successfully performed. If an image capture operation is being performed by the sensor 212 while the encoded number sleeve 300 is rotating, it is likely that any image captured would be blurred and decoding would be impaired or impossible. It is therefore advantageous for the image detection and decoding to be performed only when the encoded number sleeve 300 is stationary. This also results in a power saving relative to having the sensor 212 and LEDs 214 power on throughout a dialling operation.

In FIG. 6, a number of processes are represented schematically by rows of squares. Each square represents a short period of time, for example 0.1, 0.25 or 0.5 seconds. A black square indicates that the process is active while a white square indicates that the process is inactive. The first row, labelled "motion", represents the time for which the encoded number sleeve 300 is rotating. The second row, labelled "illumination", represents the time for which the one or more LEDs 214 are illuminating the track 304 of the encoded number sleeve 300. The third row, "image capture", represents the sensor 212 capturing one or more images of the encoded number sleeve 300 and the fourth row, "image decoding", represents the processor 202 decoding the images received from the sensor 212. The fifth row, labelled "motion detection", represents a process performed using the sensor 212 and LEDs 214 in order to determine whether or not the encoded number sleeve 300 is rotating.

When the drug delivery device 100 is turned on, which may occur automatically when the dial 108 is first rotated, the microprocessor 202 employs software stored in the ROM 204 to perform a periodic motion detection check. In embodiments where the sensor 212 is an optical sensor 212, this motion check process also requires activation of the LEDs 214 to illuminate the track 304.

At the beginning of the time sequence of FIG. 6, the encoded number sleeve 300 is rotating. The microprocessor 202 and sensor 212 perform a motion check periodically as indicated by the black squares at every fourth position in the "motion detection" row. These squares are also black in the "illumination" row, illustrating that the LED 214 is also activated at these times. For example, the sensor 212 may capture two images in quick succession while the LEDs 214 are on and the microprocessor 202 may compare the two images. If any difference between the images is detected, it may be inferred that the encoded number sleeve 300 is moving. The skilled person will be aware of other methods by which the sensor 212 can be used to determine whether the encoded number sleeve 300 is moving. As long as a discernable pattern can be seen, motion of the encoded number sleeve 300 relative to the sensor 212 can be detected.

The one or more LEDs 214 may be used in a low power state during the periodic motion detection checks. Full image clarity is not generally needed for motion detection. Therefore, when motion detection events are occurring, a lower light level is possible, resulting in further power savings. A number of extra components may be included in the circuitry 200 to allow the power levels supplied to the LEDs 214 to be adjusted. Alternatively, the LEDs 214 may function by rapidly turning on and off. The frequency of the driving signal may determine the brightness of the LEDs 214. During an image capture process, a full power state of the LEDs 214 may be used for improved clarity.

In each of the first three periodic motion detection processes, it is determined that the encoded number sleeve 300 is rotating. As a result, no image capture or decoding process is performed for the reasons previously described. The encoded number sleeve 300 ceases rotating after the third motion detection check. In the fourth motion detection check it is determined that the encoded number sleeve 300 is stationary. As a result, the LEDs 214 continue to illuminate the encoded number sleeve 300 and an image capture process is performed (squares 14-17) by the optical sensor 212.

After the image capture process is complete, the microprocessor 202 performs an image decoding process (squares 18-21). During this process, the illumination ceases and the optical sensor 212 may also be powered down to save power. At the end of the image decoding process the rotational position, and hence the dialled dose, is known. The display 210 of the drug delivery device 100 may be updated to show the currently dialled dose.

Immediately after the image decoding process is completed, the periodic motion detection check is resumed. When the motion detection check resumes and if the image decoding process was successful i.e. produced a result, then a subsequent image capture and decoding process is not performed until motion of the encoded number sleeve 300 and subsequent cessation of that motion is detected. This is illustrated in FIG. 6. The motion detection check performed immediately after the first image decoding process determines that the encoded number sleeve 300 is stationary. However, since the previous image capture and decoding process was successful, no new image capture and decoding process is performed. As it is known that no further rotation of the encoded number sleeve 300 has occurred since the previous image capture and decoding process, further power savings can be made by not performing further processes until motion is again detected.

In the third periodic motion detection check performed after the first image capture and decoding process (square 30), it is determined that the encoded number sleeve 300 is rotating. The microprocessor 202 therefore schedules a second image capture and decoding process to occur when it is next determined that the encoded number sleeve 300 is stationary.

In the fourth periodic motion detection check performed after the first image capture and decoding process (square 34), it is determined that the encoded number sleeve 300 is stationary. As a result, the LEDs 214 continue to illuminate the encoded number sleeve 300 and a second image capture process is performed (squares 35-38) by the optical sensor 212. After the second image capture process is complete, the microprocessor 202 performs an image decoding process (squares 39-42). During this process, the illumination ceases and the optical sensor 212 may also be powered down to save power. This algorithm results in the minimum number of image capture and decoding operations being required and also results in the LEDs 214 being active for the minimum period of time.

However in the example sequence of FIG. 6, during the second image capture and decoding process, further rotation of the encoded number sleeve 300 occurred (squares 36-39). In this example, the image capture and decoding process was unsuccessful due to the motion of the encoded number sleeve 300 during image capture. The microprocessor 202 therefore schedules a third image capture and decoding process to occur when it is next determined that the encoded number sleeve 300 is stationary. The periodic motion detection check resumes after the image decoding process. The motion check in square 43 detects that the encoded number sleeve 300 is stationary. As a result, the LEDs 214 continue to illuminate the encoded number sleeve 300 and a third image capture process is performed (squares 44-47) by the optical sensor 212. This is followed by a third image decoding process (squares 49-51).

Figure 7:
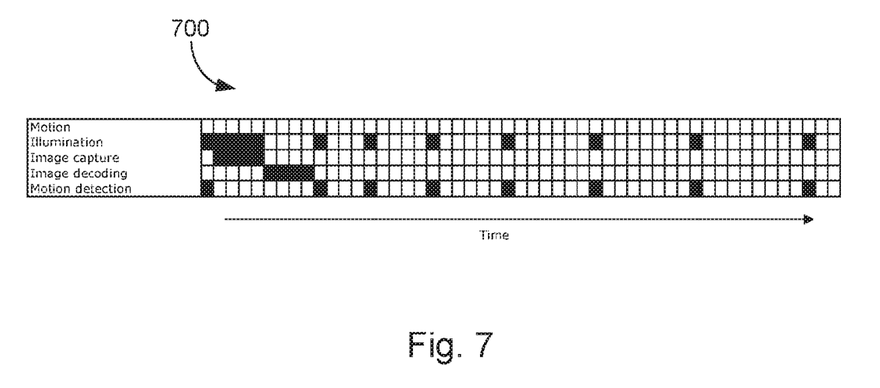
FIGS. 7 and 8 are time sequences illustrating further features of the power saving algorithm of FIG. 6.
Figure 8:
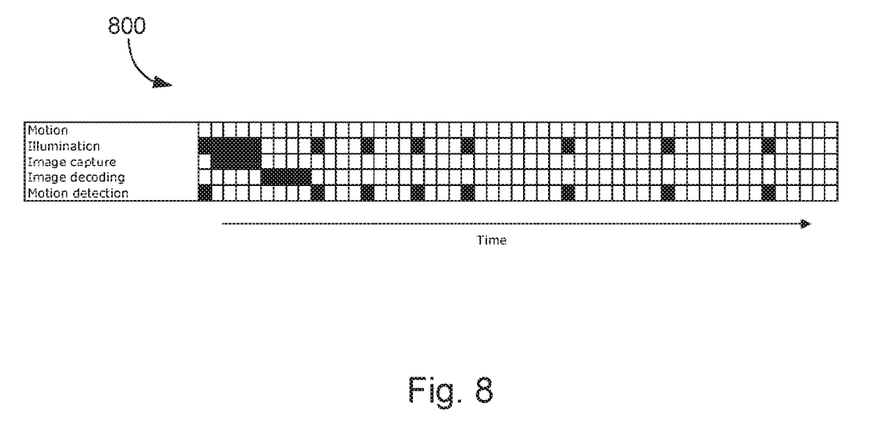

Methods of further reducing the power requirement of the drug delivery device 100 are illustrated by FIGS. 7 and 8. These figures show two different examples of how the frequency of the periodic motion detection check may be reduced when it is detected that the encoded number sleeve 300 is stationary. In the time sequence 700 of FIG. 7, the decrease in frequency of the periodic motion detection check is gradual. The first period is 4 time squares, the second is 5 time squares, the third is 6 time squares and so on. The frequency of the motion detection checks may be proportional to the length of time for which the encoded number sleeve 300 is stationary.

In the time sequence 800 of FIG. 8, the decrease in frequency of the periodic motion detection check undergoes one or more step changes. The first 4 periods are each 4 time squares and all subsequent periods are 8 time squares. In both examples, the frequency may be reduced to a minimum level (for example 8 time squares) which then remains constant. The maximum time between motion detection checks is chosen to provide maximum battery life while remaining frequent enough to react in a suitable manner to any movement of the encoded number sleeve 300. At the first instance of motion of the encoded number sleeve 300 being detected again, the frequency of the periodic motion detection check is restored to its starting level.

In embodiments of the invention which do not use an optical sensing system, the "illumination" process may be replaced with a "supply current" process. During this process electrical current is supplied to a capacitive, inductive or contact based sensing system in order to allow it to read encoded information form the encoded number sleeve 300. Similarly, the "image capture" process may be replaced with an "encoded information reading" process and the "image decoding" process may be replaced by an "encoded information decoding" process. In some embodiments, the reading and decoding of the encoded information may be intrinsically part of a single process.

The invention claimed is:

1. A method of decoding encoded information comprising optically encoded images, the method comprising:
    controlling one or more sensors to periodically check for motion of a movable component of a drug delivery device having encoded information thereon;
    if motion of the movable component is detected, preventing a first encoded information reading and decoding process from being performed;

when motion of the movable component is not detected, performing the first encoded information reading and decoding process;

the method further comprising controlling one or more light sources to illuminate the movable component of the drug delivery device during the periodic check for motion of the movable component.

2. A method of decoding encoded information according to claim 1, the method further comprising controlling the one or more light sources to illuminate the movable component of the drug delivery device during the encoded information reading process.

3. A method of decoding encoded information according to claim 2, the method further comprising controlling the one or more light sources to not illuminate the movable component of the drug delivery device during the image decoding process.

4. A method of decoding encoded information according to claim 1, further comprising, if motion of the movable component is detected subsequent to completion of the first encoded information reading and decoding process, performing a second encoded information reading and decoding process after it is detected that the motion of the movable component has ceased.

5. A method of decoding encoded information according to claim 1, wherein performing an encoded information reading and decoding process comprises:
using the one or more sensors to read the encoded information from the movable component of the drug delivery device; and
a processor receiving signals from the one or more sensors and decoding the encoded information.

6. A method of decoding encoded information according to claim 1, wherein the encoded information reading comprises capturing one or more images of the encoded images.

7. A method of decoding encoded information according to claim 4, wherein if motion of the movable component is detected during the second encoded information reading and decoding process, performing a third encoded information reading and decoding process after completion of the second encoded information reading and decoding process.

8. A method of decoding encoded information according to claim 7, wherein the third encoded information reading and decoding process is performed after a check for motion of the movable component determines that the movable component is stationary.

9. A method of decoding encoded information according to claim 1, the method further comprising resuming controlling the one or more sensors to periodically check for motion of a movable component subsequent to completion of the first encoded information reading and decoding process.

10. A method of decoding encoded information according to claim 9, wherein subsequent to completion of the first encoded information reading and decoding process, the frequency of the periodic check for motion of the movable component is dependent on the length of time for which motion of the movable component is not detected.

11. A non-transitory computer-readable storage medium having stored thereon computer-readable code, which, when executed by computing apparatus, causes the computing apparatus to decode encoded information comprising optically encoded images, where the decoding comprises:

controlling one or more sensors to periodically check for motion of a movable component of a drug delivery device having encoded information thereon;
if motion of the movable component is detected, preventing a first encoded information reading and decoding process from being performed;
when motion of the movable component is not detected, performing the first encoded information reading and decoding process;
the decoding further comprising controlling one or more light sources to illuminate the movable component of the drug delivery device during the periodic check for motion of the movable component.

12. A decoding system comprising at least one optical sensor configured to read encoded information from a movable component of a drug delivery device, one or more light sources configured to illuminate the moveable component in order to provide illumination for the optical sensor, and a processor configured to decode encoded information comprising optically encoded images, where the decoding comprises:

controlling one or more sensors to periodically check for motion of a movable component of a drug delivery device having encoded information thereon;
if motion of the movable component is detected, preventing a first encoded information reading and decoding process from being performed;
when motion of the movable component is not detected, performing the first encoded information reading and decoding process;
the decoding further comprising controlling one or more light sources to illuminate the movable component of the drug delivery device during the periodic check for motion of the movable component.

13. A decoding system according to claim 12, wherein the processor is further configured to operate the light sources in a low power state during periodic motion detection and to operate the light sources in a full power state during image capture.

14. A decoding system according to claim 12, wherein the processor is further configured to cease illumination and power down the at least one sensor during image decoding.

15. A drug delivery device comprising a housing retaining a decoding system comprising at least one optical sensor configured to read encoded information from a movable component of a drug delivery device, one or more light sources configured to illuminate the moveable component in order to provide illumination for the optical sensor, and a processor configured to decode encoded information comprising optically encoded images, where the decoding comprises:

controlling one or more sensors to periodically check for motion of a movable component of a drug delivery device having encoded information thereon;
if motion of the movable component is detected, preventing a first encoded information reading and decoding process from being performed;
when motion of the movable component is not detected, performing the first encoded information reading and decoding process;
the decoding further comprising controlling one or more light sources to illuminate the movable component of the drug delivery device during the periodic check for motion of the movable component.

* * * * *